US008518394B2

(12) United States Patent
Gazda et al.

(10) Patent No.: US 8,518,394 B2
(45) Date of Patent: Aug. 27, 2013

(54) SEAKEM GOLD AGAROSE BEADS COMPRISING ISLETS AND COATED WITH AGAROSE

(75) Inventors: Lawrence Gazda, Bellbrook, OH (US); Barry Smith, New York, NY (US)

(73) Assignee: The Rogosin Institute, New York, NY (US)

( * ) Notice: Subject to any disclaimer, the term of this patent is extended or adjusted under 35 U.S.C. 154(b) by 1168 days.

(21) Appl. No.: 11/521,977

(22) Filed: Sep. 14, 2006

(65) Prior Publication Data

US 2007/0071732 A1    Mar. 29, 2007

Related U.S. Application Data

(60) Provisional application No. 60/720,917, filed on Sep. 26, 2005.

(51) Int. Cl.
*C12N 5/07* (2010.01)
*C12N 11/10* (2006.01)
*A61K 9/14* (2006.01)
*A61F 2/00* (2006.01)

(52) U.S. Cl.
USPC ........... 424/93.7; 424/423; 424/488; 435/178

(58) Field of Classification Search
None
See application file for complete search history.

(56) References Cited

U.S. PATENT DOCUMENTS

| 4,983,268 | A | | 1/1991 | Kirkpatrick et al. |
| 5,053,332 | A | * | 10/1991 | Cook et al. ..................... 435/178 |
| 5,441,878 | A | * | 8/1995 | Thies et al. ..................... 435/178 |
| 5,643,569 | A | | 7/1997 | Jain et al. |
| 5,888,497 | A | | 3/1999 | Jain et al. |
| 5,912,005 | A | * | 6/1999 | Lanza et al. .................. 424/424 |
| 6,224,912 | B1 | | 5/2001 | Asina et al. |
| 6,303,151 | B1 | | 10/2001 | Asina et al. |
| RE38,027 | E | | 3/2003 | Jain et al. |
| 6,808,705 | B2 | | 10/2004 | Asina et al. |
| 6,818,230 | B2 | | 11/2004 | Asina et al. |
| 7,128,931 | B2 | * | 10/2006 | Leblond et al. ............... 424/490 |
| 7,413,871 | B2 | * | 8/2008 | Gazda et al. ..................... 435/29 |
| 2005/0096561 | A1 | | 5/2005 | Conn et al. |
| 2006/0121445 | A1 | | 6/2006 | Gazda et al. |

* cited by examiner

*Primary Examiner* — David M Naff
(74) *Attorney, Agent, or Firm* — Abelman, Frayne & Schwab

(57) ABSTRACT

The invention describes the manufacture and use of secretory cell containing bead structures that are coated with agarose. The beads, which are preferably 4 mm-12 mm in diameter, and which preferably contain islets, are made of a particular agarose, i.eagarose which has a sulfate content of less than 0.2 wt % but greater than zero, a pyruvate content of 0-0.1 wt %, and a Kjeldahl nitrogen content of 0-0.04 wt %. The gels found from the agarose exhibit a gel strength of at least 1200 g/cm² (1.0 wt % concentration), substantial absence of DNA binding in 0.07 M or less tris acetate buffer, and an EEO at 1.0 wt % agarose concentration of 0.05 or less.

19 Claims, 1 Drawing Sheet

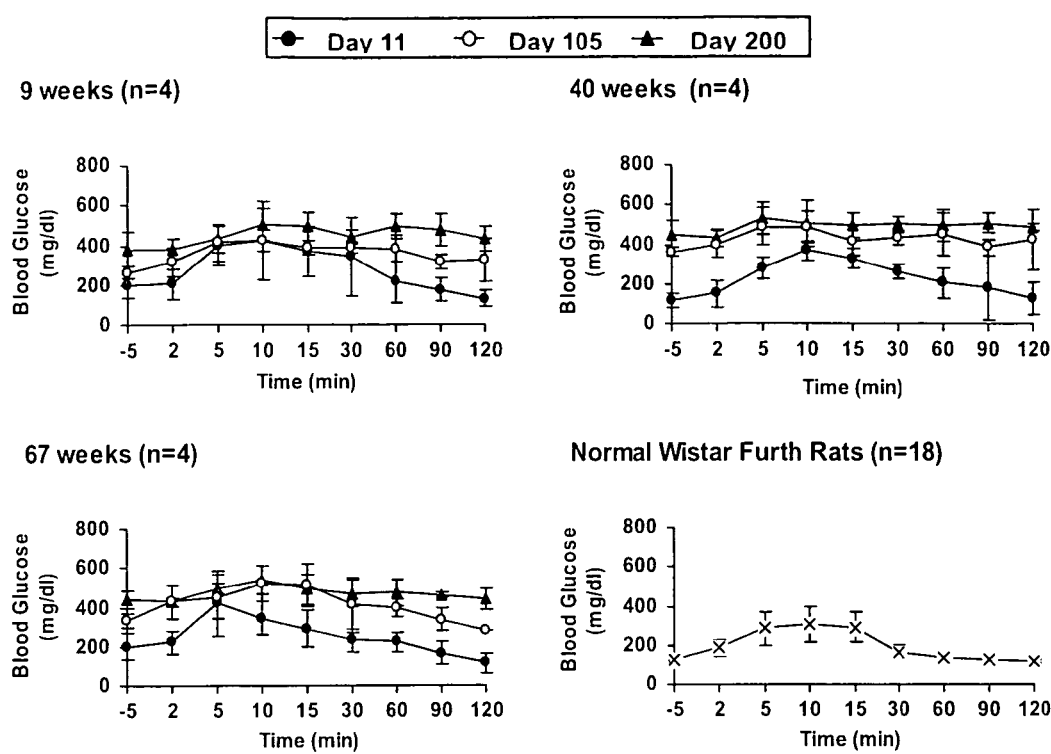

SEAKEM GOLD AGAROSE BEADS COMPRISING ISLETS AND COATED WITH AGAROSE

RELATED APPLICATIONS

This application claims priority of provisional application Ser. No. 60/629,227, filed Nov. 17, 2004, and Ser. No. 60/720,917, filed Sep. 26, 2005, incorporated by reference in their entireties.

FIELD OF THE INVENTION

This invention relates to methods for improving the quality and quantity of secretory cell containing, agarose macrobeads coated with agarose. This is accomplished via the use of a type of agarose described infra.

BACKGROUND AND PRIOR ART

It is now established that islet replacement therapy is a viable approach for treatment of patients with various disorders. These include cancer patients undergoing upper abdominal exenteration (Tzakis, et al., *Lancet* 336: 402-405 (1990)); pancreatitis (Clayton, et al., *Transplantation* 76: 92-98 (2003); Farney, et al., *Surgery* 110: 427-437 (1991); Fontes, et al., *Transplant Proc* 24: 2809 (1992); Obenholzer, et al., *Transplantation* 69: 1115-1123 (2000); Robertson, et al., *Diabetes* 50: 47-50 (2001)), and insulin-dependent patients, where islet transplantation is a therapeutic option (Goss, et al., *Transplantation* 74: 1761-1766 (2002); Ricordi, et al., *Transplantation* 75: 1524-1527 (2003); Ryan, et al., *Diabetes* 50: 710-719 (2001); Shapiro, et al., *N. Engl. J. Med* 343: 230-238 (2000)).

Due to the usefulness of islets in therapy, as is indicated, supra, there is, of course interest in developing ways to isolate them. While there are many reports on isolation of islets using the automated method (Brandhorst, et al., *Exp. Clin. Endocrinol Diabetes* 103 Suppl. 2: 3-14 (1995); Cui, et al., *Cell Transplant* 6: 48-54 (2001); Marchetti, et al., *Transplantation* 52: 209-213 (1991); Miyamoto, et al., *Cell Transplant* 7: 397-402 (1998); Nielsen, et al., *Comp. Med.* 52: 127-135 (2002); Swanson, et al., *Hum. Immunnol* 62: 73 9-749 (2001); Toomey, et al., *Brit. J. Surg.* 80: 240-243 (1993); Toso, et al., *Cell Transplant* 9: 297-305 (2000); Wennberg, et al., *Transplant. Proc.* 33: 2537 (2001)), isolation of islets remains notoriously difficult. For example, Bosta, et al., *J. Investig Med* 43: 555-566 (1995); Krickhahn, et al., *Cell Transplant* 11: 827-838 (2002); Krickhahn, et al., *Ann Transplant* 6: 48-54 (2001), O'Neil, et al., *Cell Transplant* 10: 235-246 (2001), and White, et al., *Horm. Metab. Res* 31: 579-524 (1999), all discuss problems with respect to this.

The manufacture of macrobeads which contain secretory cells and/or organelles, such as cancer cells, islets, and so forth, is well known. See, e.g., U.S. Pat. Nos. 6,818,230; 6,808,705; RE 38,027; 6,303,151; 6,224,912; 5,888,497, and 5,643,569, as well as published U.S. Patent application 2005/0096561, all of which are incorporated by reference.

Agarose is used to encapsulate the biological materials in these patent documents after which the resulting structures are further encapsulated with a second layer of agarose.

Those familiar with agarose recognize that there are many types and varieties of this material available. One such type of agarose, is described in U.S. Pat. No. 4,983,268, the disclosure of which is incorporated by reference. It has a sulfate content of less than 0.2 wt % but greater than zero, a pyruvate content of 0-0.1 wt %, and a Kjeldahl nitrogen content of 0-0.04 wt %. The gels formed from the agarose exhibit a gel strength of at least 1200 g/cm$^2$ (1.0 wt % concentration), substantial absence of DNA binding in 0.07 M or less tris acetate buffer, and an electroendosmosis (EEO) at 1.0 wt % agarose concentration of 0.05 or less.

There is an ongoing need to have improved versions of the materials first described in the patents and application set forth supra. It has now been found that use of agarose with the composition described supra results in a product that is unexpectedly superior to prior art products.

Details of the invention are set forth in the disclosure which follows:

BRIEF DESCRIPTION OF THE FIGURE

FIG. 1 sets forth information on average daily glucose levels for test and control animals.

DETAILED DESCRIPTION OF PREFERRED EMBODIMENTS

Example 1

Islets were isolated in accordance with the methodology set forth in Gazda, et al., published Patent Application 2006/0121445, published on Jun. 8, 2006, Ser. No. 11/273,737, which is incorporated by reference in its entirety. It should be kept in mind, however, that other methodologies for isolating islets are possible and may be used, as the invention is not dependent on the particular isolation method.

Following the isolation and evaluation suitable pancreases were processed further. The glands were trimmed of fat and connective tissue and then the main pancreatic duct was cannulated with a 16 g, stainless steel, and blunt end needle. A solution of HBSS containing collagenase P, at a concentration of 1.5-2.0 g/l, was perfused at a rate of 50 ml/mm, at 30° C., to provide 2 ml of solution per gram of the pancreas' weight.

The pancreas was then covered with 500 ml HBSS and 2% PS, together with 200 ml of collagenase solution, at 30° C. External circulation of water at 39° C. slowly warmed the organ to 37° C., and kept the digestate temperature at 36-37° C. When the organs appeared dissociated, and offered little resistance to manual pressure (after about 10-20 minutes total time, and 5-10 minutes after reaching 37° C.), digestion was stopped.

Collected digestate was then centrifuged, supernatants aspirated, and the resulting pellet was suspended in 10% PS and an organ preservative solution. Islets were then purified on discontinuous Ficoll, at density gradients of 1.105, 1.095, 1.085 and 1.05 g/cm$^3$, HBSS plus 2% PS, in 50 ml tubes. Tubes were centrifuged at 650 g at 4° C., and islet containing layers were collected, and washed three times, in HBSS plus 10% PS, after which they were manually purified of non-islet tissue with the aid of a dissecting microscope. The islets were resuspended, and two 0.5 ml samples were used for counting islet yield.

The average yield of ten pancreases tested was 130,000 EIN, with a mean of 1,101 EIN per gram of digested tissue. Purity, in all cases was over 90%. For 9 of the organs, islet viability was greater than 89%.

Example 2

Following the isolation of the islets, various parameters were determined, including purity and viability, as alluded to supra.

Purity was assessed by staining about 500 EIN with DTZ, for ten minutes, and then standard image analysis was carried out using a dissecting microscope and a digital camera.

Viability was determined by staining a sample with fluorescein diacetate (FDA) and ethidium bromide (EB). To elaborate, about 500 EIN were added to 1 ml of RPM1, 10% PS, and 1% antibiotic/antimyotic ("A/A"). Then, 20 µl of FDA stain that had been made with 10 mg of FDA and 1 ml acetone, and 200 µl of EB that had been made with 30 µl EB and 1 ml PBS were added. Islets were stained, in the dark, for seven minutes, and then random samples of 10-50 islets were viewed with a fluorescent microscope and photographed, to determine viability using standard image analysis.

The insulin content of the islets was also measured, by placing approximately 500 BIN in acid alcohol extraction solution (7.2 ml of 1N HCl, 400 ml of 100% denatured ethanol). Samples were stored at −20° C., and an insulin RIA was carried out.

TABLE 1

| Lot # | Insulin Content (mu/500 EIN) |
|---|---|
| W1561 | 338.66 |
| O2109 | 1288.69 |
| Y8641 | 775.37 |
| O37360 | 402.59 |
| O786 | 184.40 |
| Y8587 | 669.92 |
| W1102 | 590.05 |
| W1524 | ND |
| O39820 | ND |
| R2027 | 474.55 |

Example 3

This, and the examples which follow, address the question of whether islets identified as useful and isolated as described, can be used in macrobeads.

Purified islets were resuspended in RPMI 1640+10% PS+1% A/A, to a volume of 2000 EIN/ml. The islets were evenly distributed in tubes, so that each tube contained 1 ml of suspension at 2000 BIN.

Following settling by gravity, supernatants were removed, and 0.5 ml of 1.5% of the agarose of [0007], supra, at 50° C., prepared in minimal essential medium plus 2.5% HEPES buffer, was added to each sample, and mixed evenly. The suspension was then expelled below sterile mineral oil, to make four beads with smooth surfaces and equal islet distributions.

Macrobeads were removed, and washed twice (RPMI+5% PS+1% A/A). These macrobeads were cultured in the same solution, in a humidified 5% $CO_2$ atmosphere, for 5-7 days, after which they were washed, three times, in RPMI+1% A/A, followed by application of a second coat of agarose. For this, 0.5 ml of 5% agarose in MEM, plus HEPES buffer at 60° C., was transferred via pipette, to a sterile plastic spoon, and each macrobead was rolled 3-5 times to produce a uniform, second agarose coating. Following transfer to sterile mineral oil to produce a smooth surface, the macrobeads were removed, washed twice in RPMI+2.5% PS+1% A/A, and incubated at 37° C. in humidified 5% $CO_2$ plus air. Other methods for making the beads may, of course, be used.

The macrobeads containing encapsulated islets were determined to remain viable for more than 6 months, over which time radioimmunoassays revealed that they continued to produce good levels of insulin.

Example 4

This example describes experiments demonstrating the ability of the porcine islets to function in vivo.

Male, non-obese diabetic CB17-PrKdc <scid>/J mice, 7-9 weeks old, were used. After a week of acclimation, the animals received 275 mg/kg of streptozotocin, which induces diabetes. Nine days later, when their blood glucose levels averaged over 480 mg/dl, they were started on insulin therapy.

On day 34-35 following administration of streptozotocin, the animals received approximately 1000 EIN of porcine islets, which were transplanted in a blood clot, following Bowen et al., *Aust. J. Exp. Biol. Med. Sci.* 58:441-447 (1980), incorporated by reference. In brief, islets were pelleted out of suspension and media were aspirated. Then, about 5-10 µl of blood was taken from the animal, added to the islets, and allowed to clot. The recipient animals were anesthetized with equal volumes of ketamine (167 mg/dl), xylazine (33 mg/ml), and saline. The mixture was administered subcutaneously, at a dose of 0.5 ml/100 g. A small incision was made at the left flank to expose the kidney, and a dissecting microscope was used to make a small incision in the capsule of the kidney. The capsule was then separated from the kidney, the islets/clot were placed under the capsule, the incision was closed, and animals were permitted to recover.

Nephrectomies were performed on the animals, 38-39 days after the transplantation. Briefly, after anesthesia, the graft-bearing kidney was exposed, renal blood vessels were ligated and the kidney of each animal was removed. Five days later, the animals were sacrificed, and pancreases were collected for histological confirmation of complete islet beta cell destruction.

Tissue samples were placed in 10%, neutral buffered formation for 24 hours, and then were transferred to 70% ethyl alcohol.

Following this, the tissues were embedded in paraffin, and 5 µm sections were stained with hematoxylin and eosin. Pancreas and grafted kidney sections were stained for insulin and glucagon containing cells, using standard methods, and were then studied.

All of the mice became normoglycemic after islet grafting. After nephrectomy, the mice all became hyperglycemic, within four days.

Example 5

This example describes experiments which were designed to determine the extent to which agarose-agarose coated beads, made of different agaroses, caused tissue reaction, i.e., inflammation, in recipient animals.

Two strains of rats, i.e., Wistar and Sprague Dawley rats, were used. A total of 29 rats were tested (14 Wistar, 15 Sprague Dawley). Three rats of each strain, were used to test the agarose-agarose coated beads of the invention. Three of each strain were used to test agarose types FMC HGT(P) and Amresco. Two Wistar rats were used for testing Sigma HV agarose, as were four Sprague Dawley rats. Finally, three Wistar rats were used to test Sigma LV agarose beads, as were two Sprague Dawley rats.

A total of sixty, empty beads of each type were implanted in to the peritoneal cavities of the rats, with two exceptions. Two Sprague Dawley rats received either 54 or 59 Sigma HV agarose beads. The rats were observed for 3 months, and then sacrificed. Various organs were removed to study inflammation (spleen, liver, kidney, skeletal muscle, pancreas, and mesentery).

Tissues were evaluated by inflammation using standards approved by the American College of Veterinary Pathology. The evaluation used a 6 point scale to evaluate inflammation, essentially as follows:

0=normal
1=minimal (less than 10% inflammation)
2=mild (10-25% inflammation)
3=moderate (25-50% inflammation)
4=marked (50-75% inflammation)
5=severe (more than 75% inflammation)

The tissues for each animal were evaluated, and then averaged. The results appear below:

| Average severity scores by tissue Wistar | | | | | |
|---|---|---|---|---|---|
| | Invention | FMC HGT(P) | Sigma HV | Amresco | Sigma LV |
| Spleen | 1.0 | 1.7 | 1.3 | 1.0 | 0.7 |
| Liver | 0.0 | 0.3 | 0.3 | 1.0 | 0.7 |
| Kidney | 0.3 | 0.7 | 0.3 | 0.5 | 0.7 |
| Skeletal muscle | 0.5 | 1.3 | 1.7 | 0.0 | 2.5 |
| Pancreas | 1.7 | 1.7 | 1.3 | 2.5 | 2.0 |
| Mesentery | 2.3 | 3.0 | 2.0 | 2.5 | 3.3 |
| TOTAL | 5.8 | 8.7 | 6.9 | 7.5 | 9.9 |
| Gross Score | 19 | 36 | 25 | 24 | 20 |

| Average severity scores by tissue Sprague Dawley | | | | | |
|---|---|---|---|---|---|
| | Invention | FMC HGTP | Sigma HV | Amresco | Sigma LV |
| Spleen | 1.3 | 2.0 | 2.3 | 2.3 | 2.0 |
| Liver | 0.0 | 0.0 | 0.7 | 0.0 | 0.0 |
| Kidney | 1.0 | 0.7 | 1.0 | 1.3 | 0.0 |
| Skeletal muscle | 1.3 | 1.0 | 1.5 | 1.5 | 1.0 |
| Pancreas | 1.7 | 1.3 | 1.7 | 2.3 | 1.0 |
| Mesentery | 2.3 | 3.0 | 3.0 | 2.3 | 1.5 |
| TOTAL | 7.6 | 8.0 | 10.2 | 9.7 | 5.5 |
| Gross Score | 15 | 24 | 29 | 22 | 27 |

| Sum of average severity scores for each strain Wistar + Sprague Dawley | | | | | |
|---|---|---|---|---|---|
| | Invention | FMC HGTP | Sigma HV | Amresco | Sigma LV |
| Spleen | 2.3 | 3.7 | 3.7 | 3.3 | 2.7 |
| Liver | 0.0 | 0.3 | 1.0 | 1.0 | 0.7 |
| Kidney | 1.3 | 1.3 | 1.3 | 1.8 | 0.7 |
| Skeletal muscle | 1.8 | 2.3 | 3.2 | 1.5 | 3.5 |
| Pancreas | 3.3 | 3.0 | 3.0 | 4.8 | 3.0 |
| Mesentery | 4.7 | 6.0 | 5.0 | 4.8 | 4.8 |
| TOTAL | 13.6 | 16.6 | 17.2 | 17.2 | 15.4 |
| Gross Score | 34 | 60 | 54 | 46 | 47 |

The agarose-agarose coated beads of the invention were clearly the least inflammatory.

Additional inflammation studies were carried out on dogs, comparing the beads of the invention to beads made of FMC HGT(P) agarose (FMC HGTP agarose), and coated with it. Again, the agarose-agarose coated beads of the invention were less inflammatory.

In a further study, dogs received agarose-agarose coated beads of the invention, which contained porcine islets. The animals were sacrificed after 2.5 years, and only minimal inflammation was observed. As compared to non-implanted control animals, the peritoneum and mesentery were remarkably normal appearing.

Example 6

In these experiments, islets containing agarose macrobeads were used where the agarose used was that described in [0007], supra, which had been cultured in vitro, were compared to control (empty) macrobeads.

Islets encapsulated in the aforementioned agarose were prepared, as described in Example 3, supra.

Twelve male, spontaneously diabetic BB rats were used as subject animals. All animals were 10-15 weeks old, and had shown evidence of clinical diabetes, for 3-16 days.

At 20-21 days after arrival, the BB rats were anesthetized with ketamine/xylazine/NaCl, administered subcutaneously, at a dose of 2.2-2.3 ml/kg of body weight. Following anesthetization, the animals received either an implant of islet containing macrobeads at a dose equivalent to 1.0 times the daily insulin requirement, or a comparable number of empty macrobeads.

Following implantation, animals were observed, with clinical observations being recorded daily, including general condition (good, fair, or poor), body weight, blood glucose, urine glucose, and urine ketone. Serum samples were collected throughout the study, to be used for determining insulin, glucagon, and porcine C peptide. Radioimmunoassays were used to measure these parameters. Intraperitoneal glucose tolerance tests were also carried out.

Ninety seven days after implantation, complete necroscopies were carried out on the animals. Animals were anesthetized, and exsanguinated, and peritoneal cavities were exposed.

Throughout the 97 day period of the study, the six animals who had received the islet containing, agarose beads of the invention did not require administration of insulin. This is in contrast to animals which received empty macrobeads. These animals were administered exogenous insulin beginning two days after the start of the study, because blood glucose levels rose to 300-500 mg/dl. Two of these control animals were found dead on the third day of the study, presumably due to insulin deficiency.

Mean daily blood glucose levels were significantly lower in the animals which received the islet containing agarose beads of the invention as compared to the controls. Also, the six test animals exhibited a very narrow range of daily blood glucose deviations, even without insulin therapy.

After one month, these animals which had received the islets became moderately hyperglycemic, but exhibited limited glycemic excursions (about 100 mg/dl). This is in contrast to the controls, which showed extreme variation, of approximately 400-500 mg/dl, notwithstanding administration of 2-3 U/day of exogenous insulin.

Initial, intraperitoneal glucose tolerance tests were carried out on all animals, in order to confirm clinical diagnosis of type I diabetes. This test was also carried out 8 and 90 days after transplantations. Five days before the transplants, a response to glucose challenge was not evident, but on the eighth day after implantation, recipients of the islet containing macrobeads showed a marked response to glucose challenge, i.e., an initial rise in blood glucose, followed by a return to normoglycemia. Hyperglycemia was not inhibited as well in animals which had received the empty macrobeads, notwithstanding concurrent insulin therapy, as described, supra.

At 90 days after implantation, another intraperitoneal glucose tolerance test was performed. Baseline glycemia was again re-established for rats which had received the islet macrobeads, but starting blood glucose levels were considerably higher, i.e., approximately 400 mg/dl. Rats which had received empty macrobeads could not reestablish baseline glycemia.

The assays for porcine C-peptide did not detect the peptide in study animals prior to the implantation, or from empty macrobead recipients. In contrast, the peptide was routinely detected in the serum of rats implanted with islet macrobeads, at an average level of 0.880 0.249 ng/ml at 21 days post implant to 0.662 0.160 ng/dl at the termination of the study.

Study animals were also tested for glycosuria, ketonuria, and the need to administer bicarbonate. There were no significant differences before implantation; however, after this, islet macrobead recipients experienced significantly fewer episodes of glycosuria (37 out of 56 samples, versus 67 of 81), and ketonuria (20 of 64 samples, versus 32 of 54). The need for bicarbonate therapy was also significantly decreased (2 treatments, versus 26).

Example 7

The experiments which follow demonstrate that agarose macrobeads of the invention, which entrap islets can be cultured, in vitro, for extended periods of time, and still remain functional.

In these experiments, a set of 12 diabetic BB rats, which satisfied the same criteria as the rats in Example 6, supra, were used, as were 23 Wistar-Furth rats, 7 weeks old. This second group of rats served as normal controls.

Five of these Wistar-Furth rats were injected, through the tail vein, with 65 mg/kg of streptozotocin, to induce diabetes. When two consecutive blood glucose readings>500 mg/dl were observed, the rats began receiving insulin therapy, as described infra.

Animals were anesthetized 20-21 days after arrival, using a dose of 0.1 ml/100 g of ketamine/(60 mg/ml), xylazine (6 mg/ml)/butarphenol (3 mg/ml), administered intramuscularly.

Following anesthetization, all BB rats received agarose beads of the invention containing islets, as described supra. The rats were divided into three groups of 4, and received macrobeads that had been cultured, in vitro, for 9 weeks, 40 weeks, or 67 weeks. The amount of macrobeads administered was equivalent to 1.0× the animal's daily insulin requirement.

Five of the Wistar-Furth rats received macrobeads that had been cultured, in vitro, for 7.8-11.5 weeks, at the same dose as the BB rats. This is approximately 45-49 macrobeads per Wistar-Furth rat and 56-60 per BB rat.

Over the course of the experiments, rats gained, on the average, approximately 75 g. As a result, on day 97 following the first implant, a supplemental implant was carried out in BB rats. The average, pre-implant insulin requirement for the rats was 0.0083 U insulin/g of body weight. This value led to a calculation that an additional 17 islet containing macrobeads were needed to produce 39.19 mU of insulin per 24 hours. As is explained infra, because 4 beads were removed from each rat before the second implant, 21 macrobeads, cultured for 19 weeks, were administered. Wistar-Furth rats did not receive a second implant.

The various assays carried out in Example 7 were carried out herein as well, using the same methods.

At 201-202 days after implantation, complete necroscopies were carried out, also as described, supra.

Average daily blood glucose levels are shown in FIG. 1. Following implantation, normoglycemia (100-200 mg/dl) was restored for approximately one month in all BB rats. After this, moderate hyperglycemia (200-400 mg/dl) developed in the BB rats, and this persisted through the rest of the study. The development of moderate hyperglycemia and attainment of maximal body weight occurred contemporaneously. Body weight remained consistent, while blood glucose levels fluctuated between 300-400 mg/dl through the rest of the study. There were no differences observed in the average, daily blood glucose levels amongst the three groups of rats that received islet containing, Seakem Gold macrobeads, regardless of the length of in vitro culture time for the beads.

The Wistar-Furth rats in which diabetes had been induced also displayed normoglycemia for about a month, after which moderate hyperglycemia was observed.

It was noted, supra, that a second implant took place in BB rats, 97 days into the study. This second implant did not impact daily blood glucose values.

Porcine C peptide was also assayed, and was detected in all 3 groups of BB rats. During the first 88 days of the experiments, the average porcine C peptide level decreased from 0.6-0.9 ng/ml, to 0.2-0.4 ng/ml. At day 116, following the second implant, the peptide levels increased to an average of 0.3-0.7 ng/ml, with a 40 fold increase being observed in peritoneal fluid at necroscopy.

Glucose challenge procedures were carried out throughout the term of the study, on all rats that had received islet macrobead implants. No differences were observed in the ability of macrobeads, cultured over different lengths of time, to respond to glucose challenge after implant. To elaborate, the blood glucose levels of all BB rats had approximately doubled, from the initial value of 100-200 mg/dl. Return to baseline glycemia occurred within 120 minutes in 10 of the 12 animals. This response was similar to that observed in normal Wistar-Furth animals.

All study animals did eventually become moderately hyperglycemic, but a glucose challenge, on day 105 post-transplantation, showed an initial rise in blood glucose, and then a return to baseline glycemia. At 200 days, post-transplantation, there was only a slight increase in baseline glycemia following glucose administration and then a return to baseline glycemia.

The results in these studies, when compared to the work of Jain, et al., in Transplantation, supra, show that agarose beads containing islets prepared using agarose of [0007], supra, were unexpectedly better than those reported by Jain, et al. For example, 40% of the subject animals died by day 200, in the Jain, et al. report, while the mortality rate with the macrobeads of the invention was zero. Further, the results achieved herein were accomplished using half as many macrobeads as are reported by Jain, et al. Further, in results not elaborated on herein, following necroscopy, the production levels of insulin of retrieved macrobeads was determined, and it was substantially higher than that of the macrobeads retrieved following necroscopy as reported by Jain, et al.

Example 8

Experiments were carried out to compare the strength of the beads of the invention, to beads made and coated with FMC HGT(P) agarose.

In these tests, beads were placed, individually, in a compression device, having an upper and lower plate. The upper plate moved down, at a rate of 12 inches per minute, and beads were compressed until they ruptured. The force of the compression, (maximum compression) in lbf, was determined.

For HGT(P), the maximum compression ranged from 0.714 lbf to 3.183 lbf, with a mean of 1.958, and standard deviation of 0.5444. For the products of the invention, the range was 2.322 lbf to 6.418 lbf, with a mean of 4.282, and standard deviation of 1.096.

Clearly, the beads of the invention were stronger than those of other agarose-agarose coated beads.

The foregoing examples describe various features of the invention, which relate to secretory cell-containing agarose macrobeads, coated with agarose, where the agarose used is the agarose of [0007], supra.

As set forth herein, the term "macrobead" refers to a structure that is essentially spherical, with a diameter of from about 4 to about 10-12 mm in diameter, most preferably from about 6 to about 8 mm in diameter. The second agarose layer is preferably from about 0.05 to about 5 mm in thickness, more preferably from about 0.5 mm to about 5 mm in thickness, even more preferably, from about 1.0 to about 3 mm, and most preferably, from about 1.0 to about 2.0 mm in thickness. The second agarose layer may, but need not be, agarose in accordance with the invention.

"Macrobeads" is used as a preferred structure; however, any solid, agarose structure which encapsulates secretory cells, and is preferably coated with a second, agarose layer, are features of the invention.

The secretory cells may vary. Any cell or organelle which yields a desirable, secretory product may be encapsulated. Islets, cancer cells, and stem cells are exemplary of the types of materials which can be so used. Each bead may contain a varying number of cellular organelles, for islets, for example, from about 50 to about 5000 islets, more preferably, from about 100 to about 2500 islets, even more preferably, from about 250 to about 1000, and most preferably, from about 475 to about 550 islets. About 500 islets is most especially preferred.

Other aspects of the invention will be clear to the skilled artisan, and need not be elaborated further.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An agarose bead comprising islets, wherein the agarose of said bead has a sulfate content of less than 0.2 wt % but greater than zero, a pyruvate content of 0-0.1 wt %, and a Kjeldahl nitrogen content of 0-0.04 wt %, wherein said agarose forms a gel which has a gel strength of at least 1200 g/cm$^2$ at 1.0 wt agarose concentration, exhibits substantial absence of DNA binding in 0.07 M or less tris acetate buffer, and an electroendosmosis of 0.05 or less at 1.0 wt % agarose concentration, and said agarose bead is coated with a layer of agarose from about 0.05 mm to 5.0 mm in thickness.

2. The agarose bead of claim 1, wherein said islets are human islets.

3. The agarose bead of claim 1, wherein said islets are bovine islets.

4. The agarose bead of claim 1, wherein said islets are porcine islets.

5. The agarose bead of claim 1, containing from about 50 to about 5000 islets.

6. The agarose bead of claim 1, containing from about 100 to about 2500 islets.

7. The agarose bead of claim 1, containing from about 475 to about 550 islets.

8. The agarose bead of claim 1, wherein said agarose bead has a diameter of from about 4 mm to about 12 mm.

9. The agarose bead of claim 1, wherein said agarose bead has a diameter of from about 4 mm to about 10 mm.

10. The agarose bead of claim 1, wherein said agarose bead has a diameter of from about 4 mm to about 8 mm.

11. The agarose bead of claim 1, wherein said agarose bead has a diameter of from about 6 mm to about 8 mm.

12. The agarose bead of claim 1, wherein said agarose bead is coated with a layer of agarose from about 1.0 mm to 3.0 mm in thickness.

13. The agarose bead of claim 1, wherein said agarose bead is coated with a layer of agarose from about 1.0 mm to 2.0 mm in thickness.

14. A method of treating a subject having a condition caused by impaired functioning of islets, comprising administering the agarose bead of claim 1, in an amount sufficient to alleviate said condition.

15. The method of claim 14, wherein said condition is insulin dependent diabetes.

16. The method of claim 15, wherein said islets are human islets.

17. The method of claim 15, wherein said islets are porcine islets.

18. The method of claim 15, wherein said islets are bovine islets.

19. The method of claim 14, wherein said agarose bead is placed in the intraperitoneal cavity of said subject.

* * * * *